United States Patent
Heinz et al.

(10) Patent No.: US 10,633,341 B2
(45) Date of Patent: Apr. 28, 2020

(54) PICOLINIC ACID DERIVATIVES AND THEIR USE AS INTERMEDIATES

(71) Applicant: NOVARTIS AG, Basel (CH)

(72) Inventors: Thomas Heinz, Breitenbach (CH); Benjamin Martin, Leymen (FR); Florian Andreas Rampf, Hegenheim (FR); Werner Zaugg, Riehen (CH)

( * ) Notice: Subject to any disclaimer, the term of this patent is extended or adjusted under 35 U.S.C. 154(b) by 0 days.

(21) Appl. No.: 16/470,778

(22) PCT Filed: Dec. 18, 2017

(86) PCT No.: PCT/IB2017/058081
§ 371 (c)(1),
(2) Date: Jun. 18, 2019

(87) PCT Pub. No.: WO2018/116139
PCT Pub. Date: Jun. 28, 2018

(65) Prior Publication Data
US 2019/0345107 A1    Nov. 14, 2019

Related U.S. Application Data

(60) Provisional application No. 62/436,222, filed on Dec. 19, 2016.

(51) Int. Cl.
C07D 213/79    (2006.01)
C07D 213/81    (2006.01)

(52) U.S. Cl.
CPC ......... *C07D 213/79* (2013.01); *C07D 213/81* (2013.01)

(58) Field of Classification Search
CPC .................. C07D 213/79; C07D 213/81
See application file for complete search history.

(56) References Cited

U.S. PATENT DOCUMENTS

| 6,204,221 B1 | 3/2001 | Nebel et al. |
| 8,247,436 B2 | 8/2012 | Baettig et al. |
| 8,476,269 B2 | 7/2013 | Baettig et al. |
| 9,365,552 B2 | 6/2016 | Baettig et al. |
| RE46,757 E | 3/2018 | Baettig et al. |
| 10,117,858 B2 | 11/2018 | Baettig et al. |
| 2011/0230483 A1 | 9/2011 | Baettig et al. |
| 2014/0135329 A1 | 5/2014 | Baettig et al. |

FOREIGN PATENT DOCUMENTS

| EP | 1582524 A1 | 4/2005 |
| EP | 3153511 A1 | 4/2017 |
| WO | 1998/012179 A1 | 3/1998 |
| WO | 2007/082911 A1 | 7/2007 |
| WO | 2008/119015 A2 | 10/2008 |
| WO | 2008/138946 A1 | 11/2008 |
| WO | 2011/113894 A1 | 9/2011 |
| WO | 2013/038373 A1 | 3/2013 |
| WO | 2013/038378 A1 | 3/2013 |
| WO | 2013/038386 A1 | 3/2013 |
| WO | 2017/059085 A1 | 4/2017 |
| WO | 2017/165255 A1 | 9/2017 |

OTHER PUBLICATIONS

Notification of Transmittal of the International Search Report and the Written Opinion fo the International Searching Authority, or the Declaration, dated Mar. 1, 2018 in International Appl. No. PCT/IB32017/058081, International Filing Date: Dec. 18, 2017.
Knochel et al.: "Mixed Mg/Li amides of the type R2NMgCl.LiCl as highly efficient bases for the regioselective generation of functionalized aryl and heteroaryl magnesium compounds", Angew Chem Int Ed Engl., Apr. 28, 2006, 45(18):2958-61.
Knochel et al.:"Multiple regioselective functionalizations of quinolines via magnesiations", Org Letters, Dec. 20, 2007, ;9(26):5525-8.
Knochel et al.: "Regio- and chemoselective multiple functionalization of pyrimidine derivatives by selective magnesiations using TMPMgCl.LiCl", Org Letters, Jun. 19, 2008, 10(12):2497-500.
Knochel et al.: "Directed manganation of functionalized arenes and heterocycles using tmp2Mn + 2 MgCl2 + 4 LiCl.", Angew Chem Int Ed Engl., (2009) ;48(39):7256-60.
Knochel et al.: "Metalated N-heterocyclic reagents prepared by the frustrated Lewis pair TMPMgCl•BF3 and their addition to aromatic aldehydes and activated ketones", Chem Commun (Camb)., Mar. 14, 2013, 49(21):2124-6.

*Primary Examiner* — John M Mauro
(74) *Attorney, Agent, or Firm* — Daniel Woods

(57) ABSTRACT

The present invention relates to new picolinic acid derivatives of formula (I) and their use as intermediates in the process of making pyridine derivatives, including (S)-3-amino-6-methoxy-N-(3,3,3-trifluoro-2-hydroxy-2-methylpropyl)-5-(trifluoromethyl)picolinamide that are useful for the treatment of respiratory disorders.

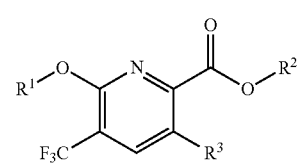

(I)

21 Claims, No Drawings

PICOLINIC ACID DERIVATIVES AND THEIR USE AS INTERMEDIATES

CROSS REFERENCE TO RELATED APPLICATIONS

This application is a U.S. National Stage Application under 35 U.S.C. § 371 of International Patent Application No. PCT/IB2017/058081, filed Dec. 18, 2017, under the Patent Cooperation Treaty (PCT), which claims the benefit of priority to U.S. Provisional Application No. 62/436,222, filed Dec. 19, 2016, the disclosure of which is incorporated by reference herein in its entirety.

FIELD OF THE INVENTION

The present invention relates to new picolinic acid derivatives of formula (I) and their use as intermediates in the process of making pyridine derivatives, including (S)-3-amino-6-methoxy-N-(3,3,3-trifluoro-2-hydroxy-2-methylpropyl)-5-(trifluoromethyl)picolinamide, useful for the treatment of respiratory disorders.

BACKGROUND OF THE INVENTION

Cystic fibrosis (CF) is a fatal genetic disease caused by mutations in the gene encoding the Cystic Fibrosis Transmembrane Conductance Regulator (CFTR), a protein kinase A activated epithelial anion channel involved in salt and fluid transport in multiple organs, including the lung. Most CF mutations either reduce the number of CFTR channels at the cell surface (e.g. synthesis or processing mutations) or impair channel function (e.g. gating or conductance mutations) or both.

PCT publication No. WO 2011/113894 describes compounds which restore or enhance the function of mutant and/or wild type CFTR for the treatment of cystic fibrosis, primary ciliary dyskinesia, chronic bronchitis, chronic obstructive pulmonary disease, asthma and other CFTR related diseases. The compounds described therein include (S)-3-amino-6-methoxy-N-(3,3,3-trifluoro-2-hydroxy-2-methylpropyl)-5-(trifluoromethyl)picolinamide (Example 5 of WO 2011/113894).

The synthesis described in WO 2011/113894 to make (S)-3-amino-6-methoxy-N-(3,3,3-trifluoro-2-hydroxy-2-methylpropyl)-5-(trifluoromethyl)picolinamide is long, uses expensive starting materials and toxic reagents. Schemes 1 and 2 outline a synthesis from WO 2011/113894 used to make (S)-3-amino-6-methoxy-N-(3,3,3-trifluoro-2-hydroxy-2-methylpropyl)-5-(trifluoromethyl)picolinamide.

Scheme 1

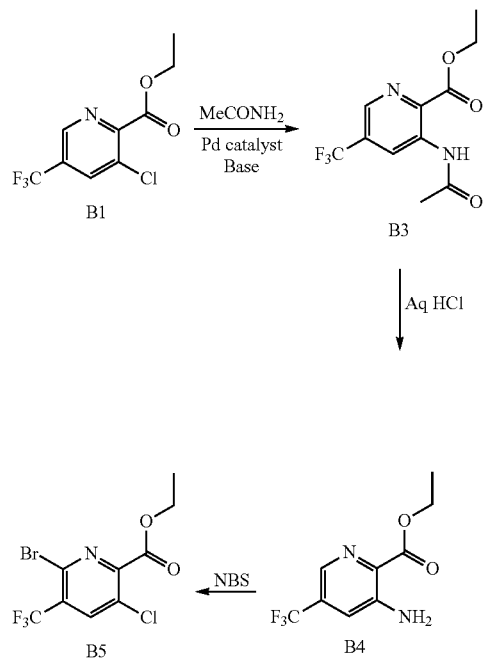

In Scheme 1, the intermediate ethyl 3-amino-5-(trifluoromethyl)picolinate (B4) is made via a Buchwald-Hartwig coupling reaction which requires the use of an expensive starting material (B1) and an expensive palladium catalyst which has to be controlled in the final product. Also, the conversion of B4 to B5 requires the use of NBS, a mutagenic reagent which has to be controlled in the API.

Scheme 2

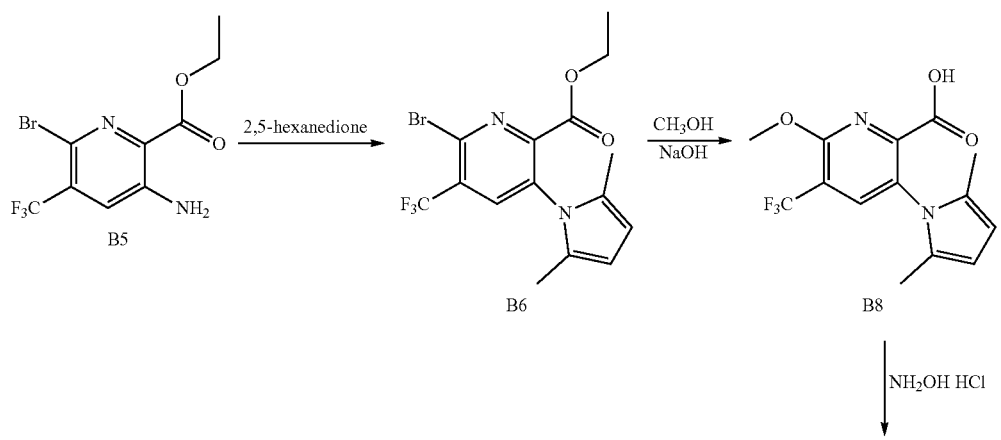

-continued

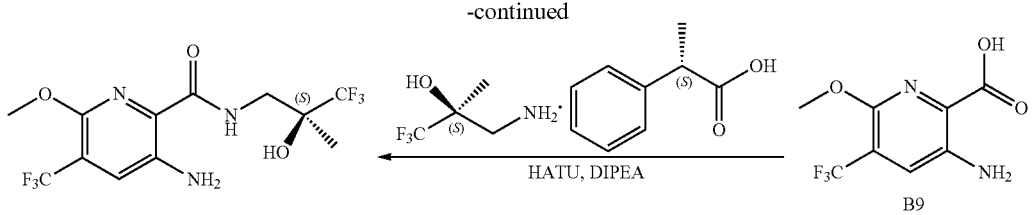

Moreover, the conversion of B5 to B8 is accomplished through the addition of 2,5-hexanedione, a well-known neurotoxin, as shown in Scheme 2. Transformation of the pyrrole in B8 to the amine B9 uses hydroxylamine which is a mutagenic and thermally unstable compound that is dangerous to use in large quantities. The overall process described in WO 2011/113894 requires many protecting group manipulations that lead to a low atom economy and afford a lot of waste. Thus there is a need for an improved synthetic process for making (S)-3-amino-6-methoxy-N-(3,3,3-trifluoro-2-hydroxy-2-methylpropyl)-5-(trifluoromethyl)picolinamide.

SUMMARY OF THE INVENTION

The present invention is directed to compounds of formula (I) and their use as intermediates in an improved process for the preparation of (S)-3-amino-6-methoxy-N-(3,3,3-trifluoro-2-hydroxy-2-methylpropyl)-5-(trifluoromethyl)picolinamide such that (S)-3-amino-6-methoxy-N-(3,3,3-trifluoro-2-hydroxy-2-methylpropyl)-5-(trifluoromethyl)picolinamide is made without the use of expensive starting materials, lengthy protecting group manipulations and toxic and unsafe materials.

DETAILED DESCRIPTION OF THE INVENTION

Embodiment 1 provides a compound according to formula (I) or a salt thereof:

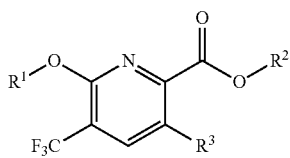

(I)

wherein
$R^1$ is $C_{1-10}$ alkyl, $C_{2-10}$ alkenyl or $C_{2-10}$ alkynyl;
$R^2$ is H, $C_{1-10}$ alkyl or benzyl; and
$R^3$ is bromo or iodo.

Embodiment 2 is the compound according to embodiment 1 wherein $R^1$ is $C_{1-10}$ alkyl.

Embodiment 3 is the compound according to embodiment 2 wherein $R^1$ is $C_{1-6}$ alkyl.

Embodiment 4 is the compound according to embodiment 3 wherein $R^2$ is $C_{1-10}$ alkyl.

Embodiment 5 is the compound according to any one of embodiments 1-4 wherein $R^2$ is $C_{1-6}$ alkyl.

Embodiment 6 is the compound according to any one of embodiments 1-5 wherein $R^2$ is $C_{1-3}$ alkyl.

Embodiment 7 is the compound according to any one of embodiments 1-6 wherein $R^2$ is methyl.

Embodiment 8 is the compound according to embodiment 1 or 2 wherein $R^2$ is H.

Embodiment 9 is the compound according to any one of embodiments 1-7 wherein $R^3$ is bromo.

Embodiment 10 is the compound 3-bromo-6-methoxy-5-(trifluoromethyl)picolinic acid or a salt thereof.

Embodiment 11 is the compound methyl 3-bromo-6-methoxy-5-(trifluormethyl)picolinate or a salt thereof.

Embodiment 12 is a process for the preparation of a compound of formula (I) or a salt thereof:

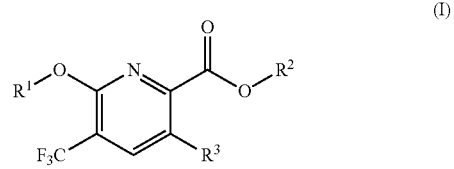

(I)

the process comprising reacting a compound of formula (II) or a salt thereof

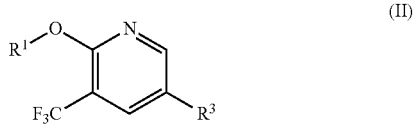

(II)

with TMPMgCl.LiCl, TMPLi, dicyclohexylamine-MgCl.LiCl, or dicyclohexylamine-Li and a reactive electrophile to obtain a compound of formula (I) or a salt thereof, wherein
$R^1$ is $C_{1-10}$ alkyl, $C_{2-10}$ alkenyl or $C_{2-10}$ alkynyl;
$R^2$ is H, $C_{1-10}$ alkyl or benzyl; and
$R^3$ is bromo, chloro or iodo.

Embodiment 13 is the process according to embodiment 12 wherein a compound of formula (II) is reacted with TMPMgCl.LiCl and a reactive electrophile to obtain a compound of formula (I).

Embodiment 14 is the process according to embodiment 12 or 13 wherein the reactive electrophile is $CO_2$, $CO(O-C_{1-10}$ alkyl$)_2$ or a chloroformate ester.

Embodiment 15 is the process according to embodiment 14 wherein the reactive electrophile is $CO_2$, $CO(O-C_{1-10}$ alkyl$)_2$, Cl—COO—$C_{1-10}$ alkyl or Cl—COOCH$_2$-phenyl.

Embodiment 16 is the process according to embodiment 15 wherein the reactive electrophile is $CO_2$ or $CO(O-C_{1-10}$ alkyl$)_2$.

Embodiment 17 is the process according to embodiment 16 wherein the reactive electrophile is $CO(OCH_3)_2$.

Embodiment 18 is the process according to embodiment 16 wherein the reactive electrophile is $CO_2$.

Embodiment 19 is the process according to embodiment 18 wherein TMEDA, DMPU, HMPA, or DMEA is added to the process.

Embodiment 20 is the process according to any one of embodiments 12-19 wherein the amount of TMPMgCl.LiCl is about 1 mole equivalent to about 5 mole equivalents based on the amount of the compound of formula (II).

Embodiment 21 is the process according to any one of embodiments 12-20 wherein the process is performed in the presence of an aprotic solvent.

Embodiment 22 is the process according to embodiment 17 or 18 wherein the solvent is THF, toluene or methyl-THF or a mixture thereof.

Embodiment 23 is the process according to any one of embodiments 12-22 wherein the process is performed at a temperature between about −50° C. and about 50° C.

Embodiment 24 is the process according to any one of embodiments 12-23 wherein $R^1$ is $C_{1-6}$ alkyl and $R^2$ is H or $C_{1-6}$ alkyl.

Embodiment 25 is the process according to any one of embodiments 12-24 wherein $R^1$ is methyl and $R^3$ is bromo.

Embodiment 26 is the process according to embodiment 12 wherein $R^1$ is methyl, $R^2$ is H or methyl and $R^3$ is bromo.

Embodiment 27 is a process for the preparation of a compound according to formula (VII)

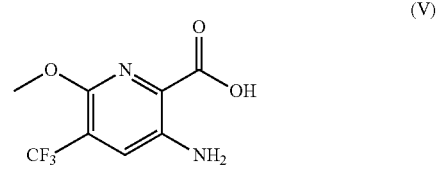 [SMILES: COc1nc(C(=O)O)c(N)cc1C(F)(F)F]

or a salt thereof, the process comprising (a) reacting a compound of formula (III) or a salt thereof with TMPMgCl.LiCl and $CO_2$

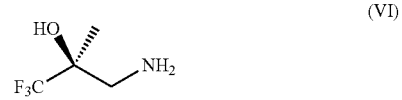

to obtain a compound of formula (IV) or a salt thereof (IV)

[structure of compound IV]

(b) under Ullmann amination conditions, converting a compound of formula (IV) or a salt thereof to a compound of formula (V)

(V)

[structure of compound V]

and (c) reacting a compound of formula (V) or a salt thereof with a compound of formula (VI) or a salt thereof (VI)

[structure of compound VI]

to obtain a compound of formula (VII) or a salt thereof and (d) optionally converting a compound of formula (VII) to a pharmaceutically acceptable salt thereof.

Embodiment 28 is the process according to embodiment 27 wherein the amount of TMPMgCl.LiCl is about 1 mole equivalent to about 5 mole equivalents based on the amount of the compound of formula (III).

Embodiment 29 is the process according to embodiment 28 wherein the amount of TMPMgCl.LiCl is about 1 mole equivalent to about 2 mole equivalents based on the amount of the compound of formula (III).

Embodiment 30 is the process according to embodiment 29 wherein TMEDA, DMPU, HMPA, or DMEA is added to Step (a) of the process.

Embodiment 31 is the process according to embodiment 30 wherein Step (a) is performed at a temperature between about −50° C. and about 50° C.

Embodiment 32 is the process according to embodiment 31 wherein Step (a) is performed at a temperature between about −50° C. and about −10° C.

Embodiment 33 is the process according to any one of embodiments 27 to 32 wherein Step (a) is performed in the presence of an aprotic solvent.

Embodiment 34 is the process according to embodiment 33 wherein the solvent is THF, toluene or methyl-THF or a mixture thereof.

Embodiment 35 is the process according to embodiment 34 where the solvent is THF or toluene.

Embodiment 36 is the process according to any one of embodiments 27-35 wherein a copper catalyst and aqueous ammonia are added to Step (b).

Embodiment 37 is the process according to any one of embodiments 27-36 wherein a copper catalyst and aqueous ammonia are added to Step (b) and then heated to a temperature of about 100° C.

Embodiment 38 is the process according to any one of embodiments 27-37 wherein HATU and diisopropyl ethylamine are added to Step (c).

Embodiment 39 is a process for the preparation of a compound according to formula (VII)

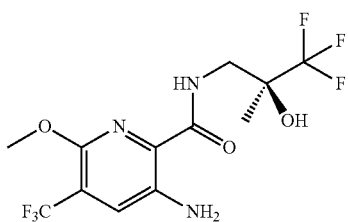

(VII)

or a salt thereof, the process comprising
(a) reacting a compound of formula (III) or a salt thereof with TMPMgCl.LiCl and CO(OCH₃)₂

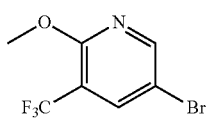

(III)

to obtain a compound of formula (VIII) or a salt thereof

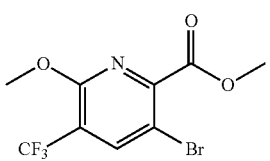

(VIII)

(b) converting a compound of formula (VIII) or a salt thereof to a compound of formula (IV) or a salt thereof

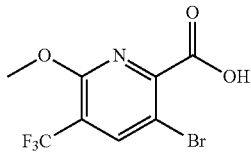

(IV)

and
(c) under Ullmann amination conditions, converting a compound of formula (IV) or a salt thereof to a compound of formula (V) or a salt thereof

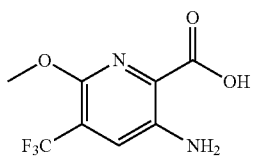

(V)

and
(d) reacting a compound of formula (V) or a salt thereof with a compound of formula (VI) or a salt thereof

(VI)

to obtain a compound of formula (VII) or a salt thereof and
(e) optionally converting a compound of formula (VII) to a pharmaceutically acceptable salt thereof.

Embodiment 40 is the process according to embodiment 39 wherein the amount of TMPMgCl.LiCl is about 1 mole equivalent to about 5 mole equivalents based on the amount of the compound of formula (III).

Embodiment 41 is the process according to embodiment 40 wherein the amount of TMPMgCl.LiCl is about 1 mole equivalent to about 2 mole equivalents based on the amount of the compound of formula (III).

Embodiment 42 is the process according to embodiment 41 wherein Step (a) is performed at a temperature between about −50° C. and about 50° C.

Embodiment 43 is the process according to embodiment 42 wherein Step (a) is performed at a temperature between about 0° C. and about 50° C.

Embodiment 44 is the process according to any one of embodiments 39 to 43 wherein Step (a) is performed in the presence of an aprotic solvent.

Embodiment 45 is the process according to embodiment 44 wherein the solvent is THF, toluene or methyl-THF or a mixture thereof.

Embodiment 46 is the process according to embodiment 45 where the solvent is THF or toluene.

Embodiment 47 is the process according to any one of embodiments 39-46 wherein a copper catalyst and aqueous ammonia are added to Step (b).

Embodiment 48 is the process according to any one of embodiments 39-47 wherein a copper catalyst and aqueous ammonia are added to Step (b) and then heated to a temperature of about 100° C.

Embodiment 49 is the process according to any one of embodiments 39-48 wherein HATU and diisopropyl ethylamine are added to Step (c).

Embodiment 50 is a process for the preparation of a compound according to formula (VII)

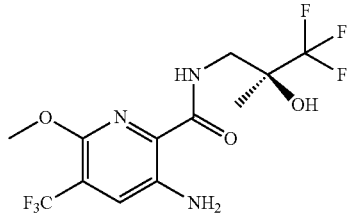

(VII)

or a salt thereof, the process comprising
(a) reacting a compound of formula (III) or a salt thereof with TMPMgCl.LiCl and a reactive electrophile

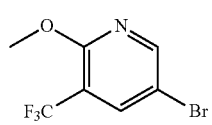

(III)

to obtain a compound of formula (X) or a salt thereof

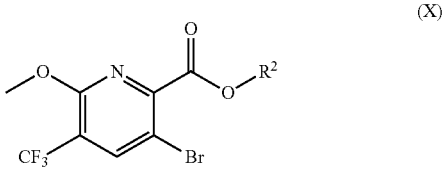

wherein $R^2$ is $C_{1-10}$ alkyl or benzyl
(b) reacting a compound of formula (X) or a salt thereof with a compound of formula (VI) or a salt thereof

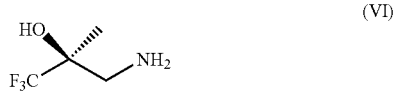

to obtain a compound of formula (IX) or a salt thereof

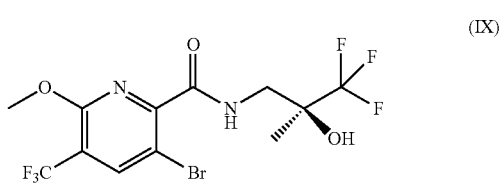 [SMILES: COc1nc(C(=O)NC[C@](C)(O)C(F)(F)F)c(Br)cc1C(F)(F)F]

(c) converting a compound of formula (IX) to a compound of formula (VII) or a salt thereof and
(d) optionally converting a compound of formula (VII) to a pharmaceutically acceptable salt thereof.

Embodiment 51 is the process according to embodiment 50 wherein the reactive electrophile is $CO(O-C_{1-10}$ alkyl$)_2$ or a chloroformate ester.

Embodiment 52 is the process according to embodiment 51 wherein the reactive electrophile is $CO(O-C_{1-10}$ alkyl$)_2$, Cl—COO—$C_{1-10}$ alkyl or Cl—COOCH$_2$-phenyl.

Embodiment 53 is the process according to embodiment 52 wherein the reactive electrophile is $CO(O-C_{1-10}$ alkyl$)_2$.

Embodiment 54 is the process according to embodiment 53 wherein the reactive electrophile is $CO(O-C_{1-3}$ alkyl$)_2$ Embodiment 55 is the process according to any one of embodiments 50-54 wherein the amount of TMPMgCl.LiCl is about 1 mole equivalent to about 5 mole equivalents based on the amount of the compound of formula (III).

Embodiment 56 is the process according to embodiment 55 wherein the amount of TMPMgCl.LiCl is about 1 mole equivalent to about 2 mole equivalents based on the amount of the compound of formula (III).

Embodiment 57 is the process according to any one of embodiments 50 to 56 wherein Step (a) is performed in the presence of an aprotic solvent.

Embodiment 58 is the process according to embodiment 57 wherein the solvent is THF, toluene or methyl-THF or a mixture thereof.

Embodiment 59 is the process according to embodiment 58 where the solvent is THF or toluene.

Embodiment 60 is the process according to any one of embodiments 50-59 wherein Step (a) is performed at a temperature between about −50° C. and about 50° C.

Embodiment 61 is the process according to embodiment 60 wherein Step (a) is performed at a temperature between about 0° C. and about 50° C.

Embodiment 62 is the process according to any one of embodiments 50-61 wherein 2,3,4,6,7,8-hexahydro-1H-pyrimido[1,2-a]pyrimidine (TBD) is added to Step (b).

Embodiment 63 is the process according to any one of embodiments 50-62 wherein a copper catalyst and aqueous ammonia are added to Step (c).

Embodiment 64 is the compound (S)-3-bromo-6-methoxy-N-(3,3,3-trifluoro-2-hydroxy-2-methylpropyl)-5-(trifluoromethyl)picolinamide or a salt thereof.

For the purposes of interpreting the terms used in the description of the invention the following definitions apply. All other terms as used herein are to be interpreted in accordance with their everyday meaning to the person of ordinary skill in the art.

As used herein, the term "alkyl" refers to a fully saturated branched or unbranched hydrocarbon chain having the specified number of carbon atoms. For example, $C_{1-10}$ alkyl refers to an alkyl group having from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecanyl, n-dodecanyl, n-tridecanyl, 9-methylheptadecanyl and the like.

As used herein, the term "alkenyl" refers to an unsaturated branched or unbranched hydrocarbon chain having the specified number of carbon atoms and one or more carbon-carbon double bonds within the chain. For example, $C_{2-10}$ alkenyl refers to an alkenyl group having 2 to 10 carbon atoms with one or more carbon-carbon double bonds within the chain. In certain embodiments alkenyl groups have one carbon-carbon double bond within the chain. In other embodiments, alkenyl groups have more than one carbon-carbon double bond within the chain. Representative examples of alkenyl include, but are not limited to, ethylenyl, propenyl, butenyl, pentenyl, hexenyl and the like. Other examples of alkenyl include, but are not limited to: Z-octadec-9-enyl, Z-undec-7-enyl, Z-heptadeca-8-enyl, (9Z, 12Z)-octadeca-9,12-dienyl, (8Z,11Z)-heptadeca-8,11-dienyl, (8Z,11Z, 14Z)-heptadeca-8,11,14-trienyl and the like.

As used herein, the term "alkynyl" refers to an unsaturated branched or unbranched hydrocarbon chain having the specified number of carbon atoms and one or more carbon-carbon triple bonds. For example $C_{2-10}$ alkynyl refers to an alkynyl group having from 2 to 10 carbon atoms with one or more carbon-carbon triple bonds within the chain. In certain embodiments alkynyl groups have one carbon-carbon triple bond within the chain. In other embodiments alkynyl groups have more than one carbon-carbon triple bond within the chain. Representative examples of alkynyl include, but are not limited to ethynyl, 1-propynyl, propargyl, butynyl, pentynyl, hexynyl and the like.

As used herein, the term "aprotic solvent" refers to any solvent which does not contain a hydrogen atom that is capable of hydrogen bonding. Examples of aprotic solvents include, but are not limited to, DMSO, DMF, toluene and THF.

As used herein, the term "copper catalyst" refers to Cu(I) or Cu(II) salts or complexes thereof. Examples include, but are not limited to, $CuSO_4$, $CuSO_4.5H_2O$, $Cu_2Br$, $Cu_2O$, and tetramine copper(II)sulfate.

As used herein, the term "reactive electrophile" refers to electrophilic compounds that can react with the metallated intermediate II. Examples include but are not limited to $CO_2$, $CO(OCH_3)_2$ and $ClCO(OCH_2CH_3)$.

As used herein, the terms "salt" or "salts" refers to an acid addition or base addition salt of a compound of the present invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of the present invention in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

The compounds of the present invention can be made through the general schemes given below.

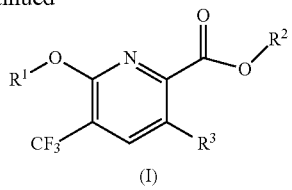

In Scheme 3, a compound of formula (I) is made via a regioselective ortho-metallation of a compound of formula (II). In step (a), a compound of formula (II) is treated with about 1 to about 5 mole equivalents of TMPMgCl.LiCl, TMPLi, dicyclohexylamine-MgCl.LiCl, or dicyclohexylamine-Li in the presence of an aprotic solvent such as DMSO, DMF, toluene or THF at a temperature of between about −50° C. and about 50° C. to form Metallated-II in situ. Optionally, TMEDA, DMPU, HMPA, or DMEA is added to the process in an amount that is about 1 to about 5 mole equivalents of the amount of a compound of formula (II), preferably about 1 to about 3 mole equivalents. In step (b), a reactive electrophile, such as $CO_2$, $CO(OCH_3)_2$ or ClCO $(OCH_2CH_3)$, is added and the final product can be isolated by extraction. Optionally the reactive electrophile, such as $CO(OCH_3)_2$, can already be present with compound (II) and reacts with the native Metallated-II in situ.

The compound of formula (I) can be used as an intermediate in the synthesis of (S)-3-amino-6-methoxy-N-(3,3,3-trifluoro-2-hydroxy-2-methylpropyl)-5-(trifluoromethyl)picolinamide (VII) as shown in Schemes 4 and 5 given below.

Scheme 4

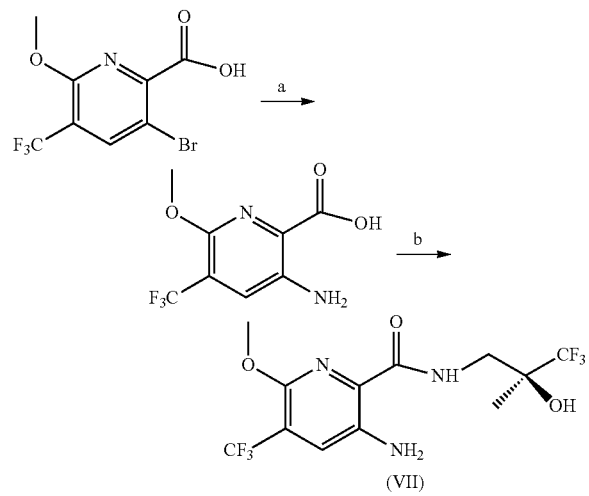

In Scheme 4, (S)-3-amino-6-methoxy-N-(3,3,3-trifluoro-2-hydroxy-2-methylpropyl)-5-(trifluoromethyl)picolinamide (VII) is produced through Step (a) where the conversion of the picoline bromine to a primary amine is accomplished by treating the picoline bromine with aqueous ammonia in the presence of a catalytic amount, for example ≤0.1 mole equivalents, of copper at a temperature of about 50° C. and about 150° C., preferably about 80° C. to 110° C. in an autoclave at 1-10 bar under inert (oxygen free) conditions ($N_2$). Formation of the final picolinic amide (VII) is accomplished by reacting the picoline amine with (S)-3-amino-1,1,1-trifluoro-2-methylpropan-2-ol using standard amide bond formation conditions, such as HATU and Hunig's Base.

Scheme 3

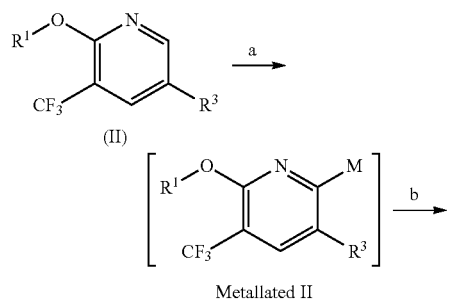

Scheme 5

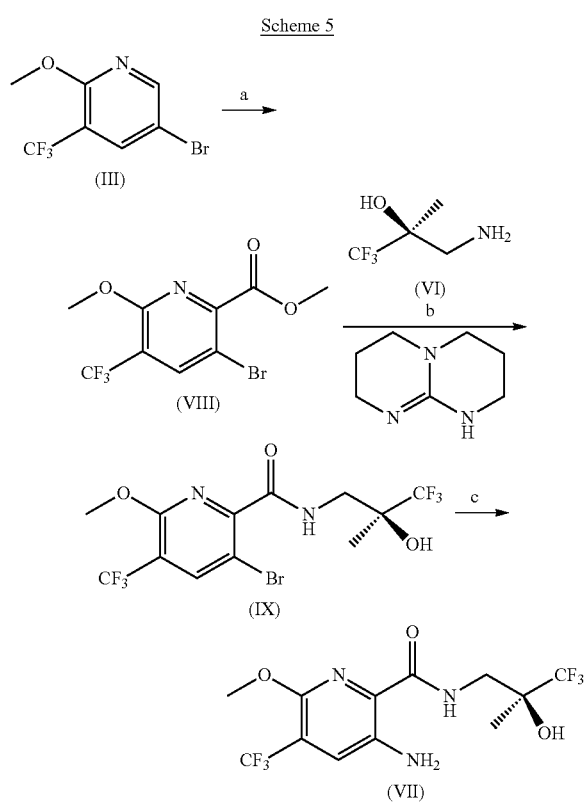

In Scheme 5, (S)-3-amino-6-methoxy-N-(3,3,3-trifluoro-2-hydroxy-2-methylpropyl)-5-(trifluoromethyl)picolinamide (VII) is produced through Step (a) where the picoline derivative (III) is treated with dimethylcarbonate and about 1 to about 5 mole equivalents of TMPMgCl.LiCl in the presence of an aprotic solvent such as DMSO, DMF, toluene or THF at a temperature of between about −50° C. and about 50° C. to form VIII. VIII is then converted to amide precursor IX through an in situ aminolysis coupling sequence in the presence of 2,3,4,6,7,8-hexahydro-1H-pyrimido[1,2-a]pyrimidine and the chiral amine. In Step (c), the final product is produced by treating the bromine of IX with aqueous ammonia in the presence of a catalytic, for example 0.1 mole equivalents, amount of copper.

As demonstrated in Schemes 3-5, compounds of formula (I) are useful intermediates in the synthesis of (S)-3-amino-6-methoxy-N-(3,3,3-trifluoro-2-hydroxy-2-methylpropyl)-5-(trifluoromethyl)picolinamide (VII). The use of these intermediates improves the process of making (S)-3-amino-6-methoxy-N-(3,3,3-trifluoro-2-hydroxy-2-methylpropyl)-5-(trifluoromethyl)picolinamide (VII) because the use and manipulation of protecting groups is eliminated. Furthermore, unlike the process in WO 2011/113894, the processes of the present invention use thermodynamically stable reagents that have minimal toxicity. The process is short and has a high atom economy and avoids a lot of waste.

Abbreviations used are those conventional in the art or the following:

Abbreviations:
API active pharmaceutical ingredient
aq aqueous
br broad
d doublet
DMEA dimethylethanolamine
DMF dimethylformamide
DMPU 1,3-dimethyl-3,4,5,6-tetrahydro-2(1H)-pyrimidinone
DMSO dimethylsulfoxide
h hour(s)
HATU 1-[bis(dimethylamino)methylene]-1H-1,2,3-triazolo[4,5-b]pyridinium 3-oxid hexafluorophosphate, N-[dimethylamino)-1H-1,2,3-triazolo-[4,5-b]pyridin-1-ylmethylene]-N-methylmethanaminium hexafluorophosphate N-oxide
HMPA hexamethylphosphoramide
HPLC high pressure liquid chromatography
HRMS high resolution mass spectrometry
kg kilogram
LCMS liquid chromatography and mass spectrometry
MS mass spectrometry
m multiplet
mg milligram
min minutes
ml milliliter
mmol millimol
m/z mass to charge ratio
NMR nuclear magnetic resonance
ppm parts per million
s singlet
t triplet
TBME methyl tert-butyl ether
THF tetrahydrofuran
TMPLi 2,2,6,6-tetramethyl-piperidinyl lithium Example 1:
3-Bromo-6-methoxy-5-(trifluoromethyl)picolinic acid

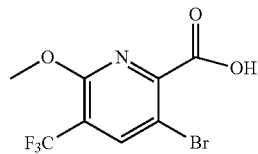

General Synthetic Scheme:

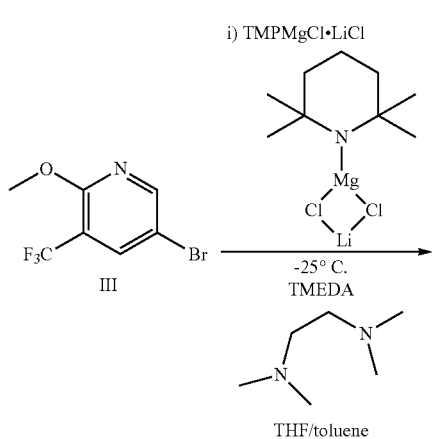

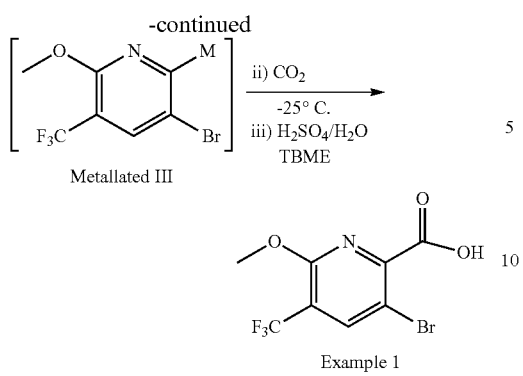

Example 1

5-bromo-2-methoxy-3-(trifluoromethyl)pyridine (III) (1.4 kg, 5.47 mol), tetramethyl ethylene diamine (TMEDA) (1.75 kg, 15 mol) and tetrahydrofuran (THF) (10 kg) were charged to a dry and inert reactor. At −25° C. a solution of 2,2,6,6-tetramethyl-piperidinylmagnesium chloride lithiumchloride complex, 1M in THF/toluene (TMPMgCl.LiCl)(14.5 kg, 15 mol) was slowly added. After stirring the reaction mixture for 30 min., $CO_2$ gas was carefully bubbled into the reactor so that the temperature of the exothermic reaction did not exceed −20° C. The reaction mixture was then quenched onto a mixture of t-butyl methyl ether (TBME) and 5% aq. $H_2SO_4$ (50 kg). The biphasic mixture was separated and the organic phase was extracted with 2M NaOH solution. The aqueous phase was acidified to pH 1-2 with 5% aq. $H_2SO_4$ and extracted with TBME. After a distillative solvent change to cyclohexane the product was crystallized from cyclohexane to yield 1.1 kg 3-bromo-6-methoxy-5-(trifluoromethyl)picolinic acid (65% yield).

$^1$H NMR (400 MHz, CDCl$_3$): δ ppm 8.24 (d, J=0.7 Hz, 1H), 4.12 (s, 3H)

$^{13}$C NMR (101 MHz, DMSO-d6): δ ppm 54.84, 106.37, 114 (m), 117.6/120.3/123.0/125.7 (m), 141.74, 152.43, 158.63, 165.63

HRMS: [M-H]$^-$ expected $C_8H_4BrF_3NO_3$, 297.9405; found $C_8H_4BrF_3NO_3$, 297.9337

Example 2: Methyl 3-bromo-6-methoxy-5-(trifluoromethyl)picolinate

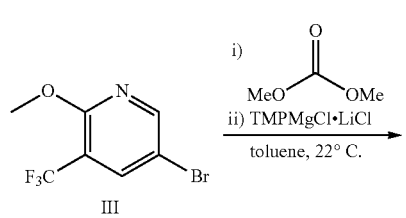

General Scheme:

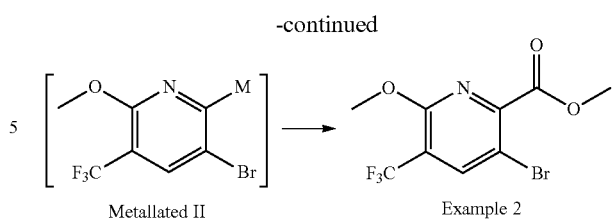

Example 2

5-bromo-2-methoxy-3-(trifluoromethyl)pyridine (III) (5.0 g, 19.53 mmol) was added to a 100 ml reactor followed by toluene (20 ml) and dimethylcarbonate (17.59 g, 195.30 mmol). To the stirred solution at 20° C. was slowly added 2,2,6,6-tetramethyl-piperidinylmagnesium chloride lithium chloride complex as a 1M solution in THF/toluene (27.34 ml, 27.34 mmol) within 45 minutes. A sample was taken and diluted in acetic acid for HPLC analysis in order to confirm full conversion of II to the methylester. Within the same vessel 5% aq. $H_2SO_4$ (36 ml) was slowly added to the reaction mixture until a pH below 2 was obtained (caution, exothermic). The biphasic mixture was separated and the lower aqueous phase back-extracted with toluene (10 ml).

In order to isolate the methylester the organic phases were combined and concentrated by rotary evaporation to yield a residue which was chromatographed on reverse-phase silica to yield the final product: methyl 3-bromo-6-methoxy-5-(trifluoromethyl)picolinate as a yellow solid, 5.3 g, 86% yield. The solid was optionally recrystallized from methanol and water to further increase purity.

$^1$H NMR (400 MHz, CDCl$_3$): δ ppm 8.08 (br s, 1H), 4.07 (s, 3H), 4.02 (s, 3H)

$^{13}$C NMR (CDCl$_3$): δ ppm 164.76, 159.22, 149.90, 141.49, 122.83, 120.12, 116.12, 108.05, 54.93, 53.09

HRMS: MH$^+$ expected $C_9H_8BrF_3NO_3$, 313.9561; found $C_9H_8BrF_3NO_3$, 313.9634

HPLC Conditions:
HPLC: Column: Agilent Zorbax SB-C18 (150 mm×3.0 mm, particle size 3.5 um)
Eluent A: Water/TFA=1000/1 (v/v)
Eluent B: Acetonitrile/TFA=1000/1 (v/v)
Wavelength: 230 nm
Flow-rate: 0.8 ml/min
Gradient: eluent B: 45% to 90% over 9 mins
Retention time 3-bromo-6-methoxy-5-(trifluoromethyl)picolinate: 5.80 min Alternative synthesis for 3-bromo-6-methoxy-5-(trifluoromethyl)picolinic acid

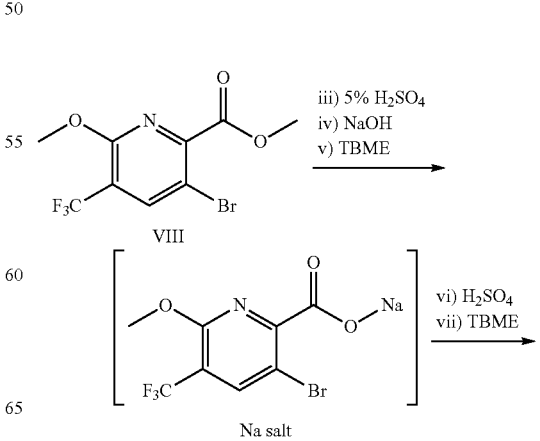

17

-continued

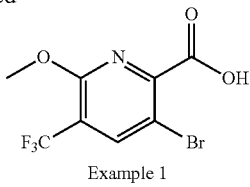

Example 1

Isolation of Example 1

In order to proceed to Example 1 without the isolation of VII, the work-up continues from the combined toluene phases post-$H_2SO_4$ quench as follows:

To the combined organic phases was slowly added 50% aq. sodium hydroxide (30 ml) until a pH of above 10 was obtained. The reaction mixture was heated to 35° C. and after 15 mins addition of water (30 ml) followed by 30 mins further stirring preceded sample-taking to ensure full hydrolysis of the methylester to Example 1 by HPLC. Water was added (130 ml), followed by TBME (60 ml) and the phases separated. To the aqueous phase was cautiously added concentrated $H_2SO_4$ (30 g) until a pH of below 2.5 was obtained (caution, exothermic and release of $CO_2$ causes foaming). TBME (100 ml) was added and the phases separated. The organic phase contained the C2, and could be evaporated to dryness by rotary evaporation to confirm the yield, 5.4 g C2, 92% yield.

$^1$H NMR (400 MHz, CDCl$_3$): δ ppm 8.24 (d, J=0.7 Hz, 1H), 4.12 (s, 3H)

$^{13}$C NMR (101 MHz, DMSO-d$_6$): δ ppm 54.84, 106.37, 114 (m), 117.6/120.3/123.0/125.7 (m), 141.74, 152.43, 158.63, 165.63

HRMS: M-H$^-$ expected $C_8H_4BrF_3NO_3$, 297.9405; found $C_8H_4BrF_3NO_3$, 297.9333

For HPLC method details see above. Retention time C2: 2.94 min

Alternative Synthesis for Ethyl 3-Bromo-6-Methoxy-5-(Trifluoromethyl)Picolinate 5-bromo-2-methoxy-3-(trifluoromethyl)pyridine (III) (0.5 g, 1.95 mmol) was added to a reactor followed by THF (2 ml) and the solution cooled to 0° C. To the mixture was added 2,2,6,6-tetramethyl-piperidinylmagnesium chloride lithium chloride complex as a 1M solution in THF/toluene (4.88 ml, 3.91 mmol), and the mixture was left to stir for 15 minutes at 0° C. An aliquot of the solution (50 ul) was then added to a reactor containing diethylcarbonate (20 ul, 19.5 mmol). A second aliquot (50 ul) was taken of the metallated II and added to a reactor containing ethyl chloroformate (14 ul, 19.5 mmol). After 2 minutes both reactors were quenched with a 1:1 mixture of acetonitrile/HCl (1M). The reaction with diethylcarbonate gave 56 A % of ethyl 3-bromo-6-methoxy-5-(trifluoromethyl)picolinate and the reaction with ethyl chloroformate gave 68 A % of ethyl 3-bromo-6-methoxy-5-(trifluoromethyl)picolinate product according to the HPLC method described above.

18

Example 3: Synthesis of (S)-3-amino-6-methoxy-N-(3,3,3-trifluoro-2-hydroxy-2-methylpropyl)-5-(trifluoromethyl)picolinamide

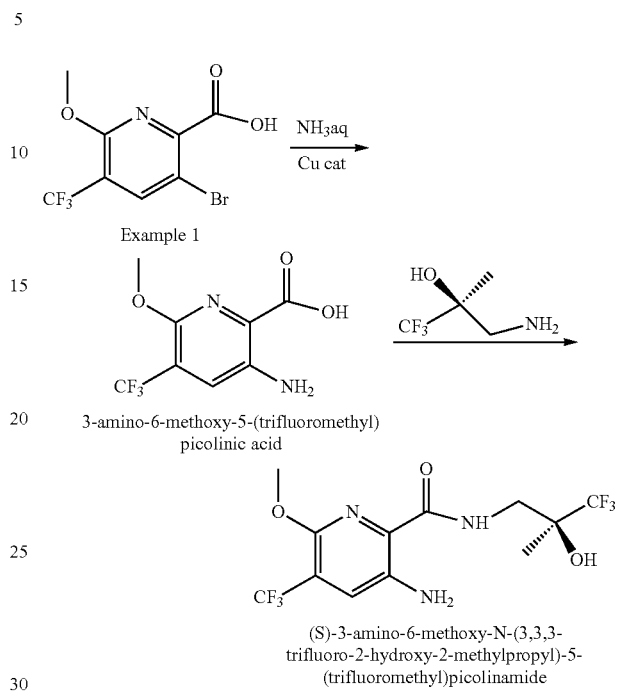

Step 1: 3-bromo-6-methoxy-5-(trifluoromethyl)picolinic acid (1.3 kg, 4.33 mol) and copper(II)sulfate pentahydrate (0.108 kg, 0.433 mol) were charged into an inert autoclave followed by aqueous ammonia 25% (12 kg). The mixture was stirred and heated up to 100° C., whereby a pressure of 7 bar resulted. The solution was stirred for 2 hr and then cooled down to 5° C. Sulfuric acid (8 M) was dosed upon cooling, so that a temperature range of 5° C. to 30° C. was held until a pH of about 5 was reached. Isopropylacetate was added and the pH was further adjusted to 1-2. The phases were separated and the organic phase was azeotropically dried by partial distillation. n-Heptane was added and the mixture stirred for 15 hr at 20° C. during which the product crystallized out. After filtration and drying 3-amino-6-methoxy-5-(trifluoromethyl)picolinic acid was obtained as a yellow solid (0.92 kg, 90%).

$^1$H NMR (400 MHz, DMSO-d6): δ ppm 7.70 (s, 1H), 3.89 (s, 3H)

$^{13}$C NMR (101 MHz, DMSO-d6): δ ppm 53.59, 116.76 m, 123.27, 126.36-117.40 m, 128.04, 142.56, 148.65, 167.62

Step 2: 3-amino-6-methoxy-5-(trifluoromethyl) picolinic acid (20 g, 84.7 mmol) and HATU (38.6 g, 101.6 mmol) were charged to a reactor followed by a solution of (S)-3-amino-1,1,1-trifluoro-2-methylpropan-2-ol in isopropylacetate (7%, 188 g, 93 mmol). The solution was stirred at room temperature, diisopropyl ethyl amine (21.9 g, 169 mmol) was added and stirring was continued for at least 16 h at 25° C. Water (250 ml) was then added dropwise within 15 min. keeping the temperature below 25° C. The water phase was separated and the organic phase was extracted with 5% aqueous HCl, 5% potassium carbonate solution, and water. The organic layer was concentrated to about 60% solution. At 50° C. n-heptane (41 g) was added and the solution was cooled by a linear ramp to 5° C. while adding more n-heptane (131 g). The precipitate was filtered off and dried at 50° C. resulting in a yellow to beige product (S)-3-amino-6-methoxy-N-(3,3,3-trifluoro-2-hydroxy-2-methylpropyl)-5-(trifluoromethyl)picolinamide (21.1 g, 69% yield).

$^1$H NMR (400 MHz, DMSO-d6): δ ppm 8.30 (m, 1H), 7.68 (s, 1H), 6.69 (s, 2H), 6.29 (s, 1H), 3.93 (s, 3H), 3.7-3.4 (m, 2H), 1.26 (s, 3H)

$^{13}$C NMR (101 MHz, DMSO-d6): δ ppm 18.92, 42.15, 53.52, 72.40, 115.5-116.5 m, 118-126 m, 122-130.7 m, 124.82, 128.3 m, 140.95, 148.49, 166.27

Example 4: Telescoped process for the synthesis of the HCl salt of 3-amino-6-methoxy-5-(trifluoromethyl)picolinic acid (V)

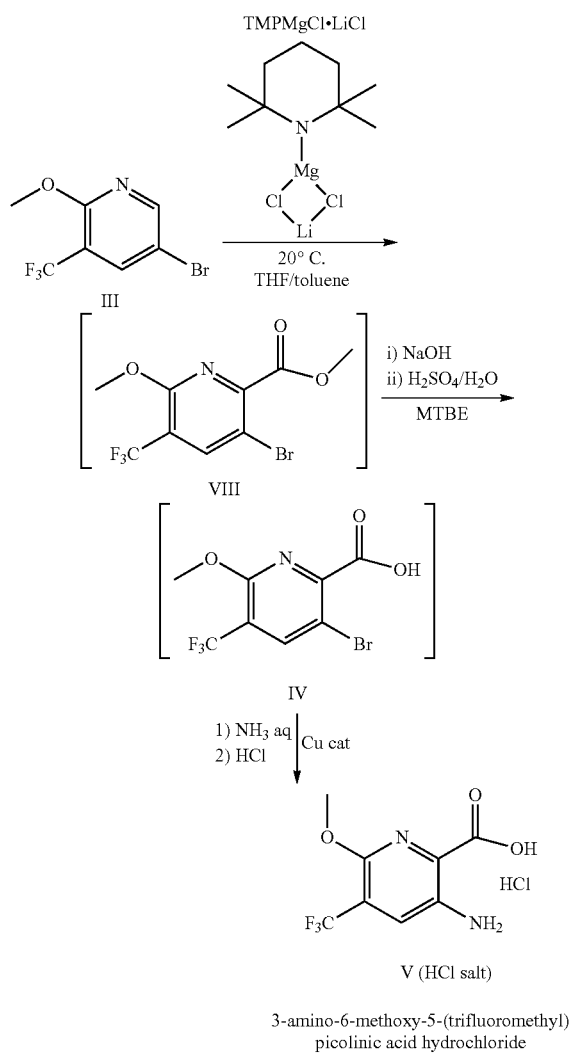

3-amino-6-methoxy-5-(trifluoromethyl) picolinic acid hydrochloride

1 Equivalent* of (III) and 6 equivalents of dimethyl carbonate (DMC) were dissolved in 3.5 parts** of toluene at room temperature. To this solution 1.5 equivalent of TMP-MgCl.LiCl solution in THF was added at 15-25° C. within ca. 1 h. Tert butyl methyl ether (MTBE, 5.9 parts) was added and the mixture was quenched in 7.3 parts of 10% sulfuric acid at 25-40° C. The water phase was discarded and to the organic phase 6.2 parts of 30% sodium hydroxide solution were added. The mixture was stirred well at 40° C. for 1-2 h. After the successful conversion of (VIII) to (IV), 2.5 parts of water were added to dissolve the partially precipitated sodium carbonate. The water phase was discarded and the organic phase was cooled to 20° C. and extracted with 4.8 parts of 25% aqueous ammonia. The aqueous phase was transferred in an autoclave and 0.0979 parts (10 mol %) of copper sulfate pentahydrate were added. The autoclave was well inertized by a pressure method and heated up to 100° C., while the pressure raises up to ca. 8 bar absolute pressure. After the successful conversion of (IV) to (V), the green solution was added to a mixture of 3.7 parts of MTBE and 6.8 parts of 50% sulfuric acid resulting in a biphasic solution of pH 1-2. The water phase was separated and the organic phase washed two times with 2.5 parts of water each. The organic phase was dried by distillation at JT 50° C./400 mbar while 3.7 parts of MTBE were added/replaced. To the dried organic solution 0.41 parts of HCl gas was dosed at 0-5° C. under or over solvent level. The suspension was stirred for ca. 1 h, then filtered off and washed with 48 parts of TBME. The product was dried at 40° C./20 mbar for ca. 12 h. (yield from (III): 72%, slightly beige solid).

*equivalents are based on the molar amount of the starting material (III)=1 equivalent
**parts=weight/weight (III)

$^1$H NMR (400 MHz, DMSO-d6): δ ppm 7.70 (s, 1H), 3.89 (s, 3H)

$^{13}$C NMR (101 MHz, DMSO-d6): δ ppm 53.59, 116.76 m, 123.27, 126.36-117.40 m, 128.04, 142.56, 148.65, 167.62

Example 5: Alternative synthesis of (S)-3-amino-6-methoxy-N-(3,3,3-trifluoro-2-hydroxy-2-methylpropyl)-5-(trifluoromethyl)picolinamide

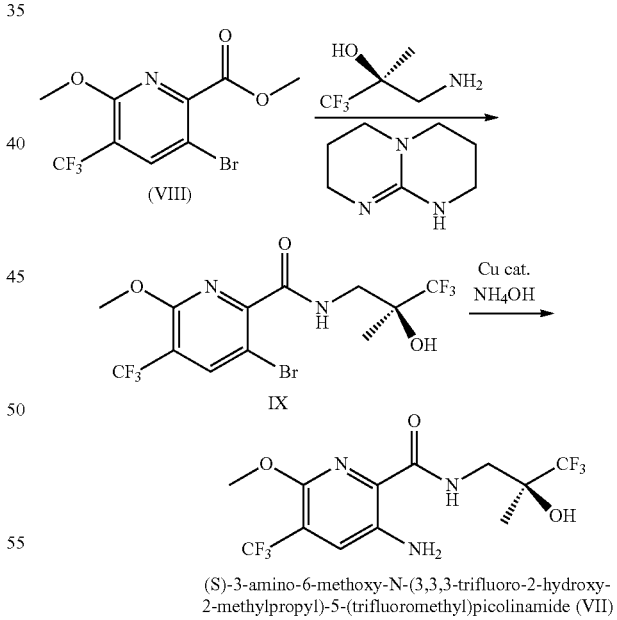

(S)-3-amino-6-methoxy-N-(3,3,3-trifluoro-2-hydroxy-2-methylpropyl)-5-(trifluoromethyl)picolinamide (VII)

Step 1: (VIII) (1.0 g), (S)-3-amino-1,1,1-trifluoro-2-methylpropan-2-ol as mandellic acid salt (1.128 g, 1.2 eq.) and 2,3,4,6,7,8-hexahydro-1H-pyrimido[1,2-a]pyrimidine (TBD, 0.588 g, 1.3 eq.) were added to a pre-dried flask as solids. To this was added the anhydrous THF (10 ml) and the cloudy solution heated to 55° C. Sampling and analytical determination of purity at 2.5 hrs confirmed 88 A% product upon which water (10 ml) was added and the phases separated. The organic phase was distilled to a concentrated mixture upon which toluene (20 ml) was added. The organic layer was extracted with 10% aq. citric acid (10 ml) followed by three consecutive extractions with 1M aq. NaOH. The organic phase was then dried with magnesium sulfate and evaporated to dryness to give 1.196 g of (S)-3-bromo-6-methoxy-N-(3,3,3-trifluoro-2-hydroxy-2-methylpropyl)-5-(trifluoromethyl)picolinamide (IX) as a white solid (95 A %, 88% yield).

$^1$H NMR, CDCl$_3$: δ ppm 8.08 (s, 1H), 7.83 (br s, 1H), 3.99 (s, 3H), 3.78-3.60 (m, 2H), 3.51 (br s, 1H), 1.36 (s, 3H)

$^{19}$F NMR, CDCl$_3$: δ ppm −64.28, −81.44

$^{13}$C DEPT135, CDCl$_3$: δ ppm 144.20 (CH), 54.70 (CH$_3$), 44.26 (CH$_2$), 19.71 (CH$_3$)

HRMS: MH$^+$ expected C$_{12}$H$_{12}$BrF$_6$N$_2$O$_3$, 424.9857; found C$_{12}$H$_{12}$BrF$_6$N$_2$O$_3$, 424.9931

HPLC (method described above): retention time=4.94 min

Step 2: IX (79 mg, 0.186 mmol) was combined with copper(II)sulfate pentahydrate (4.6 mg, 0.019 mmol), methanol (0.6 ml) and 23% aqueous ammonium hydroxide solution (559 ul) within a glass microwave vial. The headspace was inertized with nitrogen, then the vial sealed and placed in the microwave unit for heating to 105° C. for 7.5 hrs. Isopropylacetate (5 ml) was added to the deep green reaction mixture and a solvent-switch brought about by rotary evaporation. To the mixture now in water and isopropyl acetate was added 8M H$_2$SO$_4$ (5 ml), the phases mixed and then left to separate. The aqueous phase was further extracted with isopropylacetate and the combined organic phases washed with aq. NaCl (5 ml). The organic phase was dried over MgSO$_4$ and evaporated to yield of a yellow residue, 66 mg.

A portion of the residue (16 mg) was re-dissolved in heptane/ethyl acetate and submitted for combiflash purification (n-heptane/ethyl acetate gradient, elution at 20% ethyl acetate) providing (S)-3-amino-6-methoxy-N-(3,3,3-trifluoro-2-hydroxy-2-methylpropyl)-5-(trifluoromethyl)picolinamide (VII) as a residue on evaporation in 91 A % purity containing trace residual solvents (17 mg, corrected to 13 mg by $^1$H NMR, 80% yield back-calculated).

$^1$H NMR, CDCl$_3$: δ ppm 8.11 (br s, 1H), 7.37 (s, 1H), 3.97 (s, 3H), 3.76-3.72 (d, 2H, J=6.3 Hz), 1.42 (s, 3H)

$^{13}$C NMR, CDCl$_3$: δ ppm 168.86, 150.55, 140.21, 128.63, 127.26, 125.35, 124.42, 123.39, 120.68, 118.60, 74.16, 53.73, 44.39, 19.55

ESI-MS: expected mass 361.2. ELS detector, 100 A %, MH$^+$ 362.1, M$^-$ 360.1

HPLC (method described above): retention time=4.39 min

The invention claimed is:

1. A compound according to formula (I) or a salt thereof:

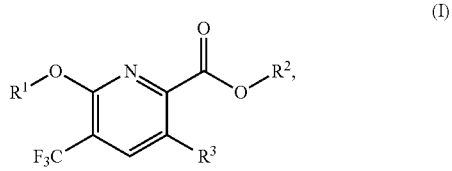

(I)

wherein
R$^1$ is C$_{1-10}$ alkyl, C$_{2-10}$ alkenyl or C$_{2-10}$ alkynyl;
R$^2$ is H, C$_{1-10}$ alkyl or benzyl; and
R$^3$ is bromo or iodo.

2. The compound according to claim 1, wherein R$^1$ is C$_{1-10}$ alkyl.
3. The compound according to claim 1, wherein R$^2$ is C$_{1-10}$ alkyl.
4. The compound according to claim 1, wherein R$^2$ is C$_{1-3}$ alkyl.
5. The compound according to claim 1, wherein R$^2$ is methyl.
6. The compound according to claim 1, wherein R$^2$ is H.
7. The compound according to claim 1, wherein R$^3$ is bromo.
8. The compound 3-bromo-6-methoxy-5-(trifluoromethyl)picolinic acid or a salt thereof.
9. The compound methyl 3-bromo-6-methoxy-5-(trifluoromethyl)picolinate or a salt thereof.
10. A process for the preparation of a compound of formula (I) or a salt thereof:

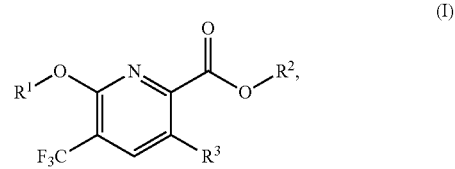

(I)

the process comprising reacting a compound of formula (II) or a salt thereof

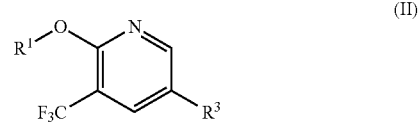

(II)

with TMPMgCl.LiCl, TMPLi, dicyclohexylamine-MgCl.LiCl, or dicyclohexylamine-Li and a reactive electrophile to obtain a compound of formula (I) or a salt thereof, wherein
R$^1$ is C$_{1-10}$ alkyl, C$_{2-10}$ alkenyl or C$_{2-10}$ alkynyl;
R$^2$ is H, C$_{1-10}$ alkyl or benzyl; and
R$^3$ is bromo, chloro or iodo.

11. A compound (S)-3-bromo-6-methoxy-N-(3,3,3-trifluoro-2-hydroxy-2-methylpropyl)-5-(trifluoromethyl)picolinamide or a salt thereof.

12. The process according to claim 10, wherein a compound of formula (II) is reacted with TMPMgCl.LiCl and a reactive electrophile to obtain a compound of formula (I).

13. The process according to claim 12, wherein the reactive electrophile is CO$_2$, CO(O—C$_{1-10}$ alkyl)$_2$, Cl—COO—C$_{1-10}$ alkyl or Cl—COOCH$_2$-phenyl.

14. The process according to claim 13, wherein the reactive electrophile is CO$_2$ or CO(O—C$_{1-10}$ alkyl)$_2$.

15. The process according to claim 12, wherein the amount of TMPMgCl.LiCl is about 1 mole equivalent to about 5 mole equivalents based on the amount of the compound of formula (II).

16. The process according to claim 10, wherein the process is performed in the presence of an aprotic solvent.

17. The process according to claim 10, wherein the process is performed at a temperature between about −50° C. and about 50° C.

18. The process according claim 10, wherein R$^1$ is methyl, R$^2$ is H or methyl and R$^3$ is bromo.

19. A process for the preparation of a compound according to formula (VII)

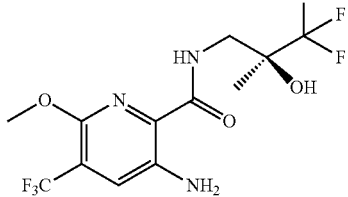
(VII)

or a salt thereof, the process comprising
(a) reacting a compound of formula (III) or a salt thereof with TMPMgCl.LiCl and $CO_2$

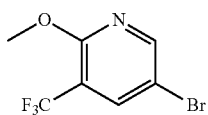
(III)

to obtain a compound of formula (IV) or a salt thereof

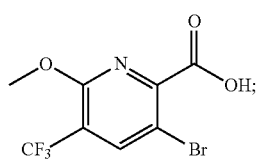
(IV)

(b) under Ullmann amination conditions, converting a compound of formula (IV) or a salt thereof to a compound of formula (V) or a salt thereof

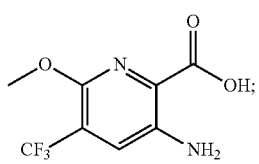
(V)

and
(c) reacting a compound of formula (V) or a salt thereof with a compound of formula (VI) or a salt thereof

(VI)

to obtain a compound of formula (VII) or a salt thereof, and
(d) optionally converting a compound of formula (VII) to a pharmaceutically acceptable salt thereof.

20. A process for the preparation of a compound according to formula (VII)

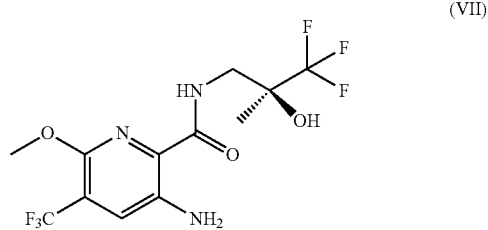 [SMILES: COc1nc(C(=O)NC[C@](C)(O)C(F)(F)F)c(N)cc1C(F)(F)F]
(VII)

or a salt thereof, the process comprising
(a) reacting a compound of formula (III) or a salt thereof with TMPMgCl.LiCl and $CO(OCH_3)_2$

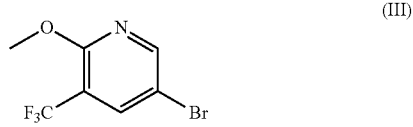
(III)

to obtain a compound of formula (VIII) or a salt thereof

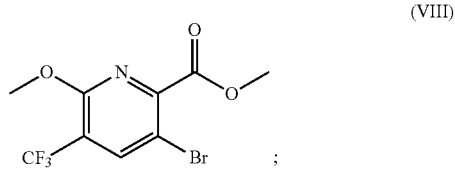
(VIII)

(b) converting a compound of formula (VIII) or a salt thereof to a compound of formula (IV) or a salt thereof

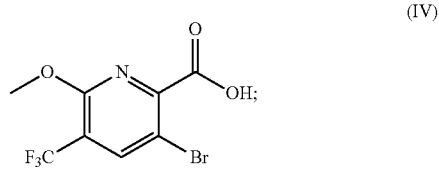 [SMILES: COc1nc(C(=O)O)c(Br)cc1C(F)(F)F]
(IV)

(c) under Ullmann amination conditions, converting a compound of formula (IV) or a salt thereof to a compound of formula (V) or a salt thereof

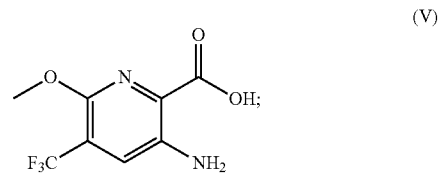 [SMILES: COc1nc(C(=O)O)c(N)cc1C(F)(F)F]
(V)

and
(d) reacting a compound of formula (V) or a salt thereof with a compound of formula (VI) or a salt thereof

(VI)

to obtain a compound of formula (VII) or a salt thereof, and (e) optionally converting a compound of formula (VII) to a pharmaceutically acceptable salt thereof.

21. A process for the preparation of a compound according to formula (VII)

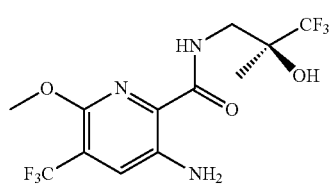

(VII)

or a salt thereof, the process comprising (a) reacting a compound of formula (III) or a salt thereof with TMPMgCl.LiCl and a reactive electrophile

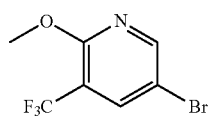

(III)

to obtain a compound of formula (X) or a salt thereof

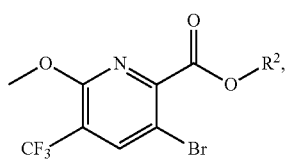

(X)

wherein $R^2$ is $C_{1-10}$ alkyl or benzyl;

(b) reacting a compound of formula (X) or a salt thereof with a compound of formula (VI) or a salt thereof

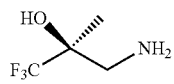

(VI)

to obtain a compound of formula (IX) or a salt thereof

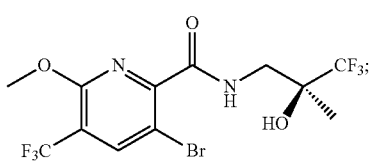

(IX)

(c) converting a compound of formula (IX) or a salt thereof to a compound of formula (VII) or a salt thereof; and (d) optionally converting a compound of formula (VII) to a pharmaceutically acceptable salt thereof.

* * * * *